(12) United States Patent
Johnson

(10) Patent No.: US 12,569,585 B2
(45) Date of Patent: Mar. 10, 2026

(54) AIR FILTRATION SYSTEM

(71) Applicant: Rexford Charles Johnson, Lake Oswego, OR (US)

(72) Inventor: Rexford Charles Johnson, Lake Oswego, OR (US)

( * ) Notice: Subject to any disclaimer, the term of this patent is extended or adjusted under 35 U.S.C. 154(b) by 295 days.

(21) Appl. No.: 16/916,377

(22) Filed: Jun. 30, 2020

(65) Prior Publication Data

US 2021/0402042 A1 Dec. 30, 2021

(51) Int. Cl.
| | |
|---|---|
| *A61L 9/20* | (2006.01) |
| *A61L 9/014* | (2006.01) |
| *B01D 53/00* | (2006.01) |
| *B01D 53/04* | (2006.01) |
| *A61L 101/02* | (2006.01) |

(52) U.S. Cl.
CPC ................ *A61L 9/20* (2013.01); *A61L 9/014* (2013.01); *B01D 53/007* (2013.01); *B01D 53/0407* (2013.01); *A61L 2101/02* (2020.08); *A61L 2209/12* (2013.01); *A61L 2209/14* (2013.01); *B01D 2253/102* (2013.01); *B01D 2253/25* (2013.01); *B01D 2257/70* (2013.01); *B01D 2259/804* (2013.01)

(58) Field of Classification Search
None
See application file for complete search history.

(56) References Cited

U.S. PATENT DOCUMENTS

| | | | | |
|---|---|---|---|---|
| 4,786,812 | A * | 11/1988 | Humphreys | .............. A61L 9/20 250/455.11 |
| 6,053,968 | A * | 4/2000 | Miller | ....................... F24F 8/22 96/16 |
| 2005/0000365 | A1 * | 1/2005 | Nelsen | ...................... A61L 9/20 96/224 |
| 2010/0143205 | A1 * | 6/2010 | Engelhard | ................ A61L 9/20 422/121 |
| 2012/0318147 | A1 * | 12/2012 | Gates | ................ B01D 53/0407 96/154 |

(Continued)

FOREIGN PATENT DOCUMENTS

| | | | | | |
|---|---|---|---|---|---|
| CN | 1185755 | A | * | 6/1998 | .............. A61L 9/20 |
| EP | 3211347 | A1 | * | 8/2017 | .............. A61L 9/22 |

(Continued)

OTHER PUBLICATIONS

Soo et al. Using UVC Light-Emitting Diodes at Wavelengths of 266 to 279 Nanometers to Inactivate Foodborne Pathogens and Pasteurize Sliced Cheese. Applied Environmental Microbiology. American Society for Microbiology. vol. 82, No. 1. pp. 11-17. https://journals.asm.org/doi/full/10.1128/AEM.02092-15 (Year: 2015).*

(Continued)

*Primary Examiner* — Jelitza M Perez
(74) *Attorney, Agent, or Firm* — Philip M. Weiss; Weiss & Weiss

(57) ABSTRACT

An air filtration system which pulls air into and through the air filtration system filter where the air is exposed to a UV lamp that provides UV light, the UV lamp surrounded by an internally polished aluminum shield or other device made of a material that reflects or enhances kill ability of microorganisms when exposed to UV light.

13 Claims, 5 Drawing Sheets

(56)  References Cited

U.S. PATENT DOCUMENTS

| | | | | |
|---|---|---|---|---|
| 2014/0212327 A1* | 7/2014 | Fink | .......................... | A61L 9/20 |
| | | | | 422/4 |
| 2015/0078960 A1* | 3/2015 | Krosney | ............. | B01D 53/007 |
| | | | | 422/4 |
| 2018/0236121 A1* | 8/2018 | Worrilow | ............... | B01D 53/02 |
| 2019/0063763 A1* | 2/2019 | Kleinberger | ............ | A61L 2/022 |
| 2019/0308122 A1* | 10/2019 | Aries | ................. | B01D 46/0049 |

FOREIGN PATENT DOCUMENTS

| | | | | | |
|---|---|---|---|---|---|
| WO | WO-9637281 A1 * | 11/1996 | ............... | A61L 9/20 |
| WO | WO-2011138569 A1 * | 11/2011 | ............. | A61L 9/205 |

OTHER PUBLICATIONS

Bruno et al. WO2011138569A1—translated document (Year: 2011).*
Disanayaka et al. CN1185755A—translated document (Year: 1998).*
WO2011138569A1—translated document (Year: 2011).*

* cited by examiner

—10

—20

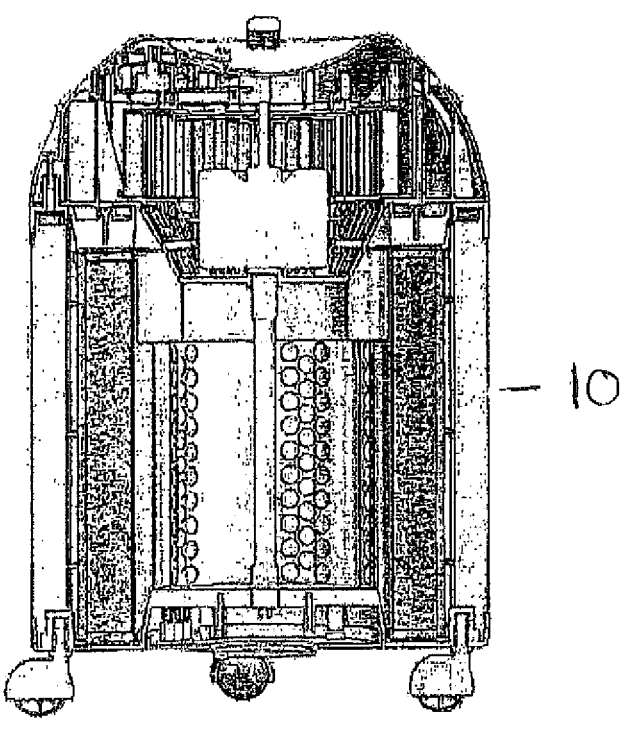
— 10
Fig. 3
Fig. 4
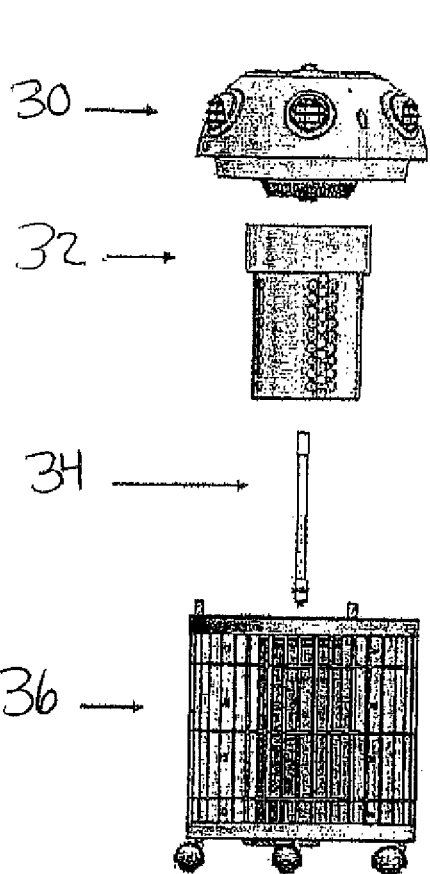
30 →
32 →
34 →
36 →

85

81

90 Airflow from UV Shield to fan

98 "Choke" Point for airflow

92 Airflow from Inner Wall Ring

96 Airflow Holes of Outer Wall

94 Airflow Holes of Inner Wall

AIR FILTRATION SYSTEM

FIELD OF THE INVENTION

The present invention relates to an air filtration system which pulls air into the air filtration system filter where the air is exposed to a polished aluminum shield or other device made of a material that controls or enhances the reflection of the UV wavelength coming from the UV lamp that enhances kill ability of micro-organisms that are introduced to it.

BACKGROUND OF THE INVENTION

US patent publication 20060034737 relates to an air purifier held in a housing with an ambient air inlet and an air outlet, defining an airflow path therethrough for treating ambient air. A filter is disposed in the airflow path that has an air permeable media for communicating air therethrough while retaining particles carried in the flow of air. A purification device attaches to an intermediate chassis in the airflow path for treating the air moved by a fan into operative engagement with the purification device within the housing and out the air inlet. A controller operates the purification device by sensing an operative status of the purification device.

US patent publication 20070059225 relates to a germicidal ultraviolet apparatus mounted within a specially designed filter element designed to fit within the standard filter access ports for re-circulating HVAC air systems. The UV light source is positioned to project UV light towards surfaces within the filter area and components found downstream of the filter in the HVAC system for the purpose of sterilization and maintenance of these areas. The filter elements contain a special tackified air filtration media designed to increase reactivity of the UV light within the filter area. A safety interlock mechanism cuts power to the UV source when the filter element is removed from the re-circulating air system. Various sources of supplying power to the UV apparatus are used for installation flexibility.

US patent publication 20190117820 relates to a personal air treatment device used to treat air with UV irradiation and with scents. The scents may be used as an attractant or masking for hunting. Multiple devices may be controlled by a smartphone application to strategically alter scent dispersion according to local wind patterns, user location and device location. Similar air treatment devices may be integrated with a particulate mask or used to treat the air around a user.

US patent publication 20190257314 relates to a combination axial fan and LED lighting system to fit into the footprint of a standard ceiling tile. Ceiling tiles may have a built-in fan and/or LED lighting. The system may include a housing container and an axial fan. The fan has a fan cavity including air diversion mechanism to direct air from the fan cavity toward the lighting and fan components. It further includes an airflow surface to direct air exiting the fan cavity along an LED light fixture. Also included is one or more UV light sources which irradiate contaminants as air flows through the ceiling.

SUMMARY OF THE INVENTION

The present invention relates to an air filtration system that works by pulling air into the air filtration system filter. The air filtration system draws air into the air filtration system through the air filtration system filter at 360°, equally spaced around the vertical structure of the air filtration system using a structural design that allows maximum airflow of the air filtration system.

To provide maximum air cleaning solutions, the air flows through the multi-layer design of the air filtration system filter which comprises a compressed carbon structure of a specialized activated carbon with a specific particle size that is impregnated with a potassium permanganate mixture which is used to help remove any aldehyde molecules such as formalin, formaldehyde, glutaraldehyde and other volatile materials. Finally, the air filtration system filter's external surfaces are surrounded by an antimicrobial material to help trap and capture large particles to improve the carbon air filtration system filter ability to work more efficiently. The air filtration system filter is designed to adsorb thousands of different chemicals and other smaller particles to ensure that clean air particle-free and chemical-free air exits the filter.

The air filtration system pulls air through the air filtration system filter so that the air flows into the interior area of the air filtration system filter chamber and is exposed to a shield that surrounds the UV lamp and is made of a material that controls and enhances the reflection of the UV wavelength enhancing kill ability of micro-organisms that are introduced to it.

It is an object of the present invention for the shield that surrounds the UV lamp to be comprised of aluminum with the internal part of the shield being a polished aluminum. Polished aluminum is aluminum that is shinier and enhances the reflective ability or index of the aluminum. This UV light has a very specific wavelength to help kill and render micro-organisms such as mold, yeast, fungus, spores, endospores, bacteria, and viruses non-contagious. The purpose of the internal polished aluminum shield is to control and enhance the reflection of the UV wavelength enhancing kill ability when micro-organisms are introduced to it. The preferred UV light wavelength, C wavelength, is approximately 254 nm.

It is an object of the present invention for the air to flow through the air filtration system through ports on the top of the air filtration system. It is an object of the present invention for there to be six exit ports and for the exit ports to be re-positioned at any angle when the air leaves the air filtration system.

It is an object of the present invention for the air filtration system to be controlled by a dimmer on-off switch to allow the operator multiple different speeds when using the air filtration system.

The present invention relates to an air filtration system having a fan/motor housing assembly, a UV lamp, a shield that surrounds the UV lamp and is made of a material that controls and enhances the reflection of the UV wavelength enhancing kill ability of micro-organisms that are introduced to it, a base assembly and a filter. The UV lamp has its own electrical assembly.

It is an object of the present invention for the UV shield to be made of aluminum where the inside of the shield that faces the UV lamp comprises polished aluminum.

It is an object of the present invention for the air filtration system filter and other internal components to be protected from UV light by a double wall polished aluminum shield. It is an object of the present invention for the air filtration system to comprise offset holes to allow airflow through the UV shield.

It is an object of the present invention for the UV shield to have outer wall air holes and inner wall air holes that surround the UV lamp. It is an object of the present invention for off-set holes to minimize UV exposure of the air filtration system carbon filter while allowing airflow.

The present invention relates to an air filtration system, where air flows from the room into the air filtration system filter and passes through the outer wall holes of the polished aluminum UV shield. Air flows through the inner holes of the polished aluminum UV shield and is exposed to UV light. UV sterilized air flows through the air flow cap and fan. Clean air then flows out of the vents and into the room. It is an object of the present invention for the polished aluminum shield to seal against the gasket contained in the air filtration system filter to prevent airflow from coming up.

It is an object of the present invention for air to flow from the polished aluminum UV shield to the fan, air to flow from the inner wall ring, air flow from holes of the inner wall, air flow from holes of the outer wall and the choke point for airflow.

It is an object of the present invention for the polished aluminum UV shield to have handles. It is an object of the present invention for the handles to be integrated into the top area of the UV shield. Because the polished aluminum shield and air filtration system filter are in such close contact, by lifting the polished aluminum shield, the air filtration system filter is also lifted up.

BRIEF DESCRIPTION OF THE DRAWINGS

FIG. 3 is an internal side view of the air filtration system of the present invention.

FIG. 4 is an un-assembled view of the air filtration system of the present invention.

DETAILED DESCRIPTION OF THE INVENTION

Figure 1:
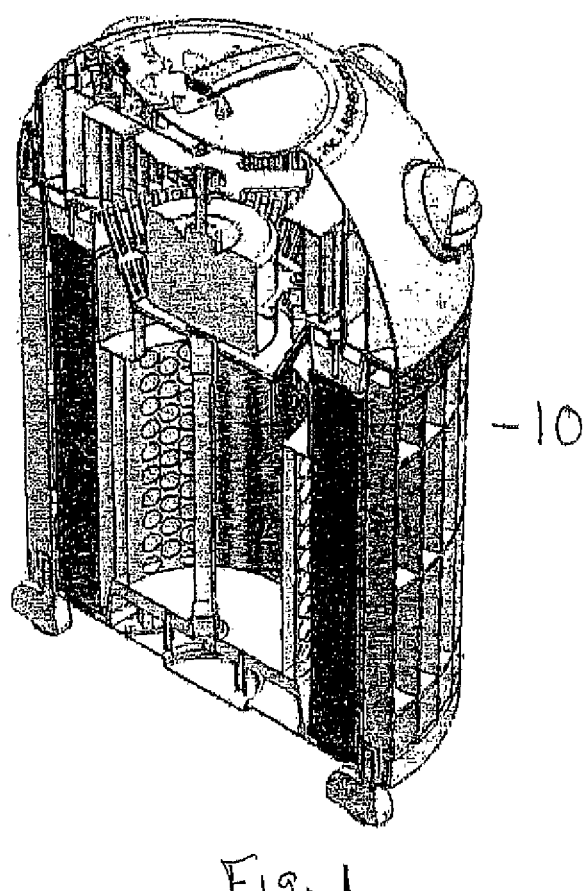
FIG. 1 illustrates a top side view of the air filtration system of the present invention.

FIG. 1 is a top internal side view of the air filtration system 10.

Figure 2:
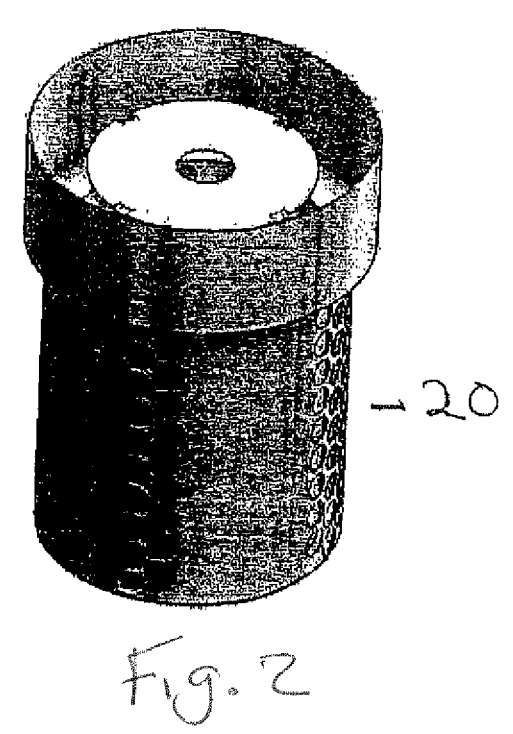
FIG. 2 is a top side view of the internally polished aluminum UV shield of the present invention.

FIG. 2 is a top side view of the internally polished aluminum UV shield 20, of the present invention.

FIG. 3 is a side view of the air filtration system 10.

FIG. 4 is an unassembled view of the air filtration system 10 having a fan housing assembly 30, a UV shield 32 made of internally polished aluminum, a UV lamp 34 and a base assembly and filter 36.

Figure 5:
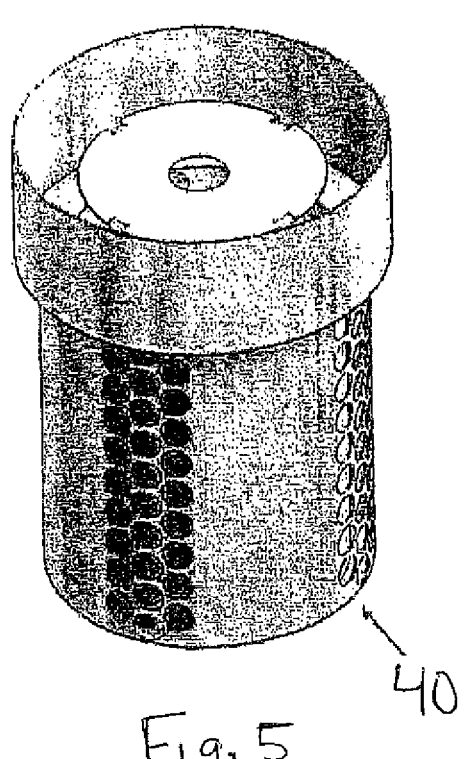
FIG. 5 is a top side view of the internally polished aluminum UV shield of the present invention.

FIG. 5 shows an internally polished aluminum UV shield 40.

Figure 6:
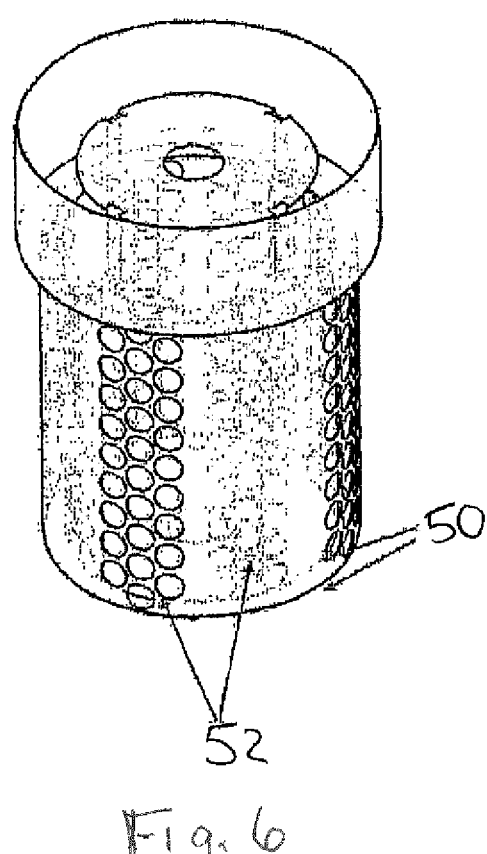
FIG. 6 is an internal view of the internally polished aluminum UV shield of the present invention.

FIG. 6 shows a double wall internally polished aluminum shield 50 that protects the air filtration system filter and other internal components from UV, and offset holes 52 to allow airflow.

Figure 7:
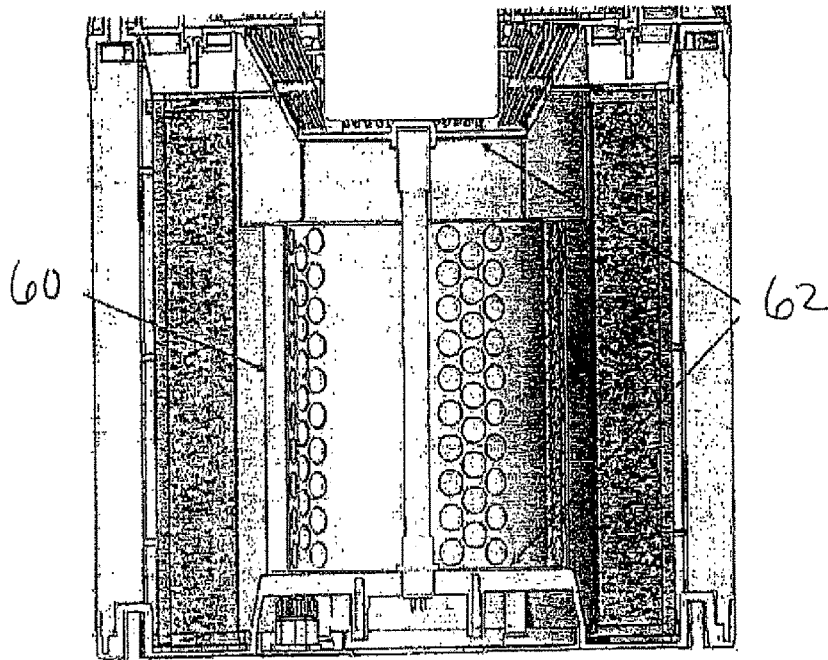
FIG. 7 is an internal side view of the internally polished aluminum UV shield of the present invention within the air filtration system.

FIG. 7 shows the UV shielding comprising internally polished aluminum shield 60 and plastic shielding 62 that protects the top and bottom of the air filtration system.

Figure 8:
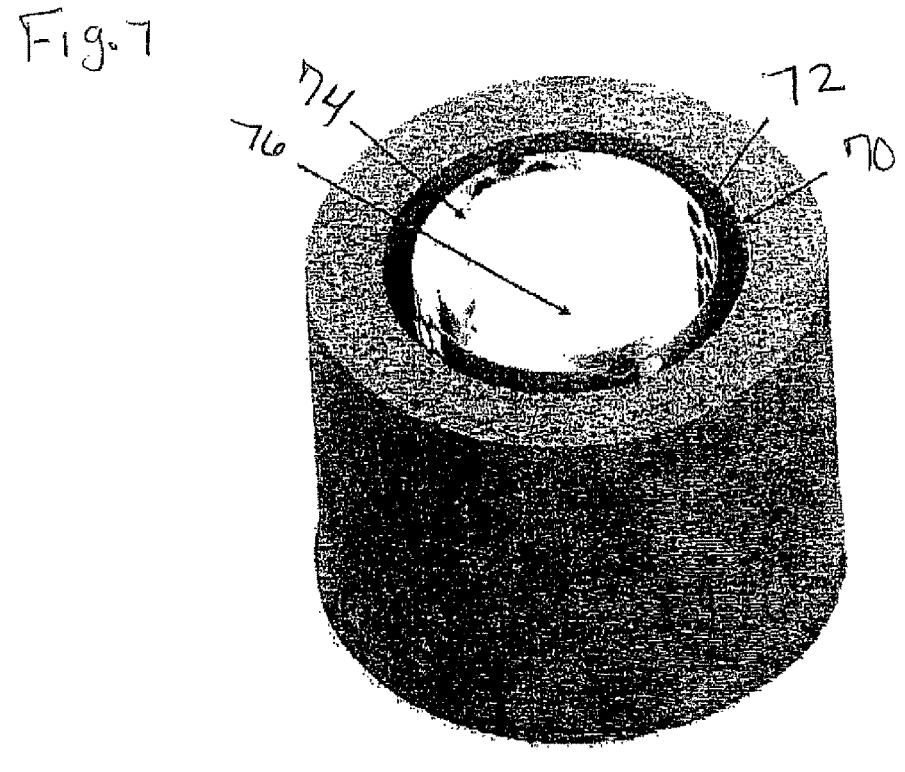
FIG. 8 is a horizontal cross section view of the internally polished aluminum UV shield and air filtration system filter of the present invention.

FIG. 8 shows a horizontal top side cross section of the carbon filter 70, and an internally polished aluminum UV shield having outer wall air holes 72 and inner wall air holes 74 that surround a UV lamp 76. The off-set holes minimize UV exposure to the filter 70 and other internal components while allowing airflow.

Figures 9, 10:
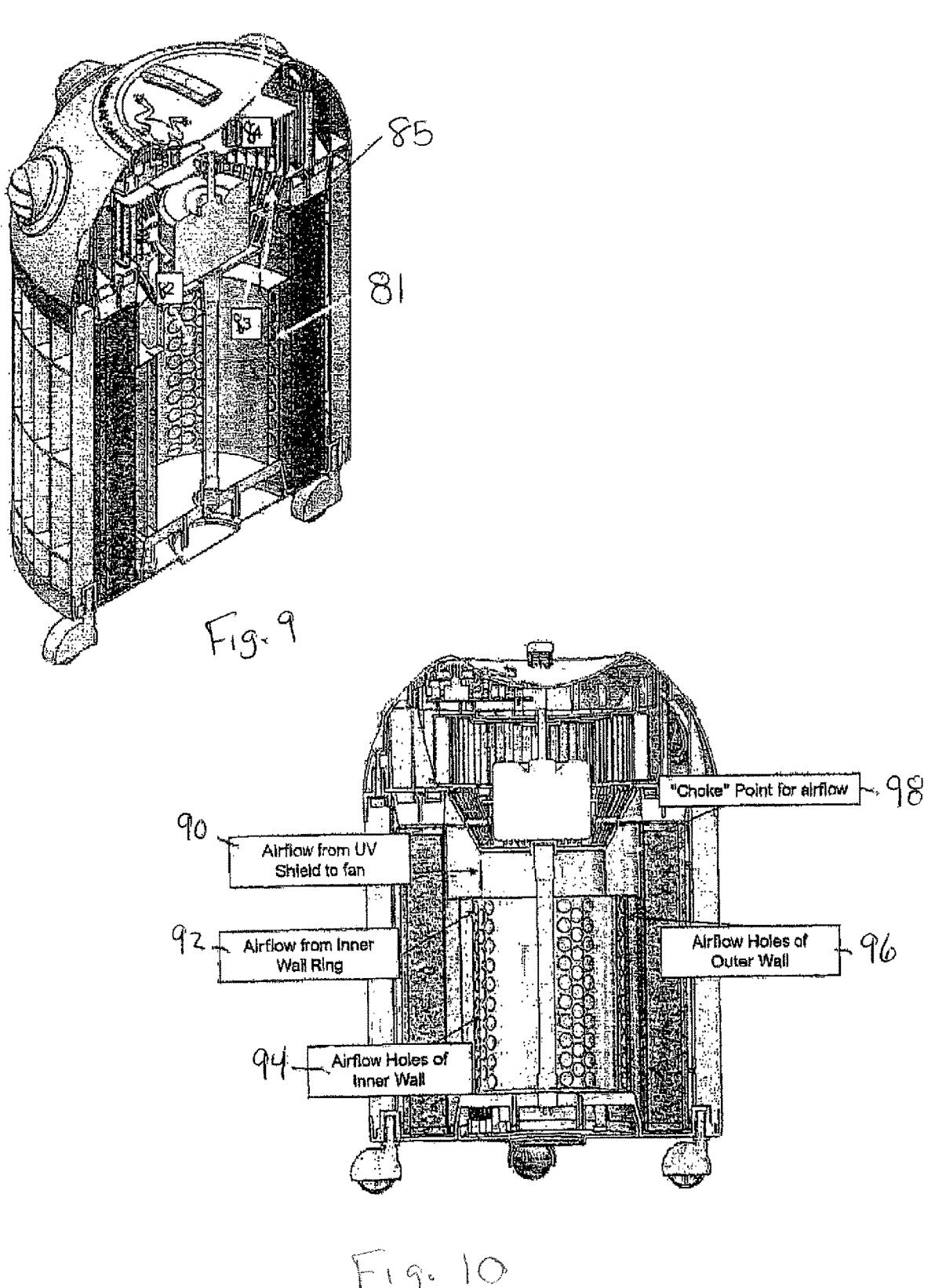
FIG. 9 is an internal top side view of the air filtration system of the present invention.
FIG. 10 is an internal side view of the air filtration system of the present invention.

FIG. 9 shows the air flow of the air filtration system 10. As shown by arrow 81, air flows from the room into the air filtration system filter and passes through the outer wall holes of the internally polished aluminum UV shield. As shown by arrow 82, air flows through the inner holes of the internally polished aluminum UV shield and is exposed to UV light. As shown by arrow 83, UV sterilized air flows through the air flow cap and fan.

As shown by arrow 84, clean air flows out of vents and into the room. 85 shows how the internally polished aluminum shield seals against the gasket to prevent airflow from coming up.

FIG. 10 shows the airflow from the internally polished aluminum UV shield to the fan 90, the airflow from the inner wall ring 92, the airflow from holes of the inner wall 94, the airflow from holes of the outer wall 96 and the choke point for airflow 98.

In order to match the airflow without the internally polished aluminum UV shield installed, the minimum air flow area must be found. The airflow through the internally polished aluminum UV shield must be equal or greater than this point. The minimum air flow area from the choke point is 24.7 inches squared. The airflow area of the outer wall holes is 35.6 inches squared. The airflow area from the inner wall holes is 28.3 inches squared. The airflow area from the inner wall ring is 24.7 inches squared. The airflow area from the internally polished aluminum UV shield to the fan is 24.7 inches squared.

The invention claimed is:

1. An air filtration system comprising:
   an air filtration system that pulls air into an air filtration system filter at 360° equally spaced around vertical structure of said air filtration system;
   said air filtration system filter comprised of a compressed carbon structure of activated carbon impregnated with potassium permanganate to remove aldehyde molecules that are selected from formalin, formaldehyde, glutaraldehyde and other volatile aldehyde materials;
   said air filtration system filter having external surfaces surrounded by an antimicrobial material that traps and captures particles improving said air filtration system filter to work more efficiently;
   a shield made of a material that controls and enhances the reflection of UV wavelength enhancing kill ability of micro-organisms that are introduced to it;
   said shield surrounding a UV light lamp;
   wherein UV light from said UV lamp has a wavelength that kills or renders micro-organisms non-contagious; and
   ports which air flows through on top of said air filtration system which are re-positioned at any angle when air leaves said air filtration system.

2. The air filtration system of claim 1 wherein said shield is made of aluminum and the internal surface of said shield is made of polished aluminum.

3. The air filtration system of claim 1 wherein said air filtration system filter adsorbs thousands of different chemicals and other smaller particles.

4. The air filtration system of claim 1 wherein said wavelength is 254 nm.

5. The air filtration system of claim 1 wherein said micro-organisms consist of mold, yeast, fungus, spores, endospores, bacteria, and viruses.

6. The air filtration system of claim 1 wherein said air filtration system is controlled by a dimmer on-off switch to allow an operator multiple different speeds when using said air filtration system.

7. An air filtration system comprising:

a UV lamp;

a UV shield made of a material that controls or enhances reflection of UV wavelength enhancing kill ability of micro-organisms introduced to it;

said UV shield comprised of an internally polished aluminum shield;

said UV shield comprising a double wall, wherein said double wall comprises an outer wall and an inner wall, wherein said outer wall comprises outer wall air holes and said inner wall comprises inner wall air holes, and said outer wall air holes and said inner wall air holes surround said UV lamp;

a fan/motor housing assembly;

a base assembly; and a filter;

said UV lamp provides UV light that has a wavelength that kills or renders micro-organisms non-contagious.

8. The air filtration system of claim 7 wherein said filter is comprised of a compressed carbon structure of activated carbon impregnated with potassium permanganate to remove aldehyde molecules.

9. The filter of claim 7 wherein said filter is surrounded by antimicrobial material.

10. The air filtration system of claim 7 wherein said UV lamp provides said UV C light wherein said wavelength is approximately 254 nm.

11. The air filtration system of claim 7 wherein the outer wall air holes and the inner wall air holes are offset in said shield to allow airflow out of said system;

said offset holes minimize UV exposure of said filter and other internal components while allowing for airflow.

12. The air filtration system of claim 7 further comprising plastic shielding located above and below said UV lamp that protects top and bottom of said air filtration system.

13. The air filtration system of claim 7 wherein said UV shield has handles integrated into said UV shield.

\* \* \* \* \*